(12) United States Patent
Romeis et al.

(10) Patent No.: US 7,918,893 B2
(45) Date of Patent: Apr. 5, 2011

(54) HINGED ORTHOPAEDIC PROSTHESIS

(75) Inventors: Kristen L. Romeis, Warsaw, IN (US);
Matthew D. Smith, Akron, IN (US);
Allan Ritchie, Harrogate (GB)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/865,030

(22) Filed: Sep. 30, 2007

(65) Prior Publication Data
US 2009/0088860 A1    Apr. 2, 2009

(51) Int. Cl.
*A61F 2/38* (2006.01)
(52) U.S. Cl. .................................... 623/20.24
(58) Field of Classification Search .... 623/20.14–20.33, 623/21.11, 18.11, 21.13, 21.15, 21.16, 16.11, 623/11.11
See application file for complete search history.

(56) References Cited

U.S. PATENT DOCUMENTS

| | | | |
|---|---|---|---|
| 3,852,830 A | 12/1974 | Marmor | |
| 3,869,729 A | 3/1975 | Attenborough | |
| 3,953,899 A | 5/1976 | Charnley | |
| 3,958,278 A | 5/1976 | Lee et al. | |
| 4,034,418 A | 7/1977 | Lee et al. | |
| 4,219,893 A | 9/1980 | Noiles | |
| 4,224,697 A | 9/1980 | Murray et al. | |
| 4,340,978 A | 7/1982 | Buechel et al. | |
| 4,790,853 A * | 12/1988 | Engelbrecht et al. | 623/20.25 |
| 4,838,891 A | 6/1989 | Branemark et al. | |
| 5,314,481 A * | 5/1994 | Bianco | 623/20.25 |
| 5,370,701 A | 12/1994 | Finn | |
| 5,413,607 A * | 5/1995 | Engelbrecht et al. | 623/20.24 |
| 5,766,257 A | 6/1998 | Goodman et al. | |
| 5,824,096 A | 10/1998 | Pappas et al. | |
| 5,824,102 A * | 10/1998 | Buscayret | 623/20.21 |
| 5,871,541 A | 2/1999 | Gerber | |
| 5,951,603 A | 9/1999 | O'Neil et al. | |
| 5,954,770 A | 9/1999 | Schmotzer et al. | |
| 6,019,794 A * | 2/2000 | Walker | 623/20.22 |
| 6,074,424 A * | 6/2000 | Perrone et al. | 623/20.3 |
| 6,117,175 A * | 9/2000 | Bosredon | 623/20.15 |
| 6,264,696 B1 * | 7/2001 | Reigner et al. | 623/20.24 |
| 6,319,283 B1 | 11/2001 | Insall et al. | |
| 6,482,209 B1 | 11/2002 | Engh et al. | |

(Continued)

FOREIGN PATENT DOCUMENTS

DE    2901009    7/1980

(Continued)

OTHER PUBLICATIONS

FDA Document, KA-012255, Richards Mod II Knee, 56 pgs, 1976.

(Continued)

*Primary Examiner* — Alvin J. Stewart
(74) *Attorney, Agent, or Firm* — Barnes & Thornburg LLP (57) ABSTRACT

An orthopaedic prosthesis includes a tibial bearing, a femoral component, and a hinge post coupled to the tibial bearing and the femoral component. The hinge post includes a medial and lateral axle. A pair of bushings are coupled to the axles and received in an internal chamber of the femoral component. The prosthesis may also include a plug received in the internal chamber and positioned to secure the hinge post to the femoral component. The femoral component is configured to rotate about an axis defined by the axles. In some embodiments, the femoral component may include a housing and a patella bearing separate from the housing.

22 Claims, 11 Drawing Sheets

U.S. PATENT DOCUMENTS

| | | | | |
|---|---|---|---|---|
| 6,485,519 | B2 * | 11/2002 | Meyers et al. | 623/20.24 |
| 6,488,711 | B1 * | 12/2002 | Grafinger | 623/20.24 |
| 6,652,587 | B2 | 11/2003 | Felt et al. | |
| 6,660,039 | B1 | 12/2003 | Evans et al. | |
| 6,709,461 | B2 | 3/2004 | O'Neil et al. | |
| 6,723,102 | B2 | 4/2004 | Johnson et al. | |
| 6,755,864 | B1 * | 6/2004 | Brack et al. | 623/20.29 |
| 6,764,516 | B2 * | 7/2004 | Pappas | 623/20.29 |
| 6,770,097 | B2 * | 8/2004 | Leclercq | 623/20.15 |
| 6,773,461 | B2 * | 8/2004 | Meyers et al. | 623/20.24 |
| 6,827,739 | B2 * | 12/2004 | Griner et al. | 623/16.11 |
| 6,972,039 | B2 * | 12/2005 | Metzger et al. | 623/20.29 |
| 6,984,249 | B2 * | 1/2006 | Keller | 623/20.24 |
| 7,115,131 | B2 | 10/2006 | Engh et al. | |
| 7,232,465 | B2 * | 6/2007 | Keller | 623/20.24 |
| 7,303,586 | B2 * | 12/2007 | Keller | 623/20.29 |
| 7,326,252 | B2 * | 2/2008 | Otto et al. | 623/20.15 |
| 7,572,292 | B2 * | 8/2009 | Crabtree et al. | 623/20.24 |
| 7,591,855 | B2 * | 9/2009 | Keller | 623/20.24 |
| 7,615,081 | B2 * | 11/2009 | Justin et al. | 623/20.14 |
| 7,658,767 | B2 * | 2/2010 | Wyss | 623/20.29 |
| 2001/0003803 | A1 * | 6/2001 | Leclercq | 623/20.29 |
| 2001/0018615 | A1 * | 8/2001 | Biegun et al. | 623/20.35 |
| 2001/0021877 | A1 * | 9/2001 | Biegun et al. | 623/20.28 |
| 2001/0034554 | A1 * | 10/2001 | Pappas | 623/20.29 |
| 2001/0034555 | A1 * | 10/2001 | Pappas | 623/20.29 |
| 2002/0058997 | A1 * | 5/2002 | O'Connor et al. | 623/20.32 |
| 2002/0103541 | A1 | 8/2002 | Meyers et al. | |
| 2002/0120340 | A1 * | 8/2002 | Metzger et al. | 623/20.15 |
| 2002/0138150 | A1 | 9/2002 | Leclercq | |
| 2002/0156535 | A1 * | 10/2002 | Pappas | 623/20.29 |
| 2002/0183850 | A1 | 12/2002 | Felt et al. | |
| 2003/0009228 | A1 * | 1/2003 | Meyers et al. | 623/20.24 |
| 2003/0009229 | A1 * | 1/2003 | Pappas | 623/20.27 |
| 2003/0009230 | A1 * | 1/2003 | Gundlapalli et al. | 623/20.28 |
| 2003/0009231 | A1 * | 1/2003 | Gundlapalli et al. | 623/20.29 |
| 2003/0171815 | A1 * | 9/2003 | Kana et al. | 623/20.15 |
| 2003/0208276 | A1 * | 11/2003 | Berelsman et al. | 623/20.11 |
| 2004/0006393 | A1 * | 1/2004 | Burkinshaw | 623/20.3 |
| 2004/0039450 | A1 * | 2/2004 | Griner et al. | 623/20.31 |
| 2004/0054416 | A1 * | 3/2004 | Wyss et al. | 623/20.27 |
| 2004/0083003 | A1 * | 4/2004 | Wasielewski | 623/20.21 |
| 2004/0102851 | A1 * | 5/2004 | Saladino | 623/20.15 |
| 2004/0102852 | A1 * | 5/2004 | Johnson et al. | 623/20.15 |
| 2004/0162620 | A1 * | 8/2004 | Wyss | 623/20.27 |
| 2004/0186584 | A1 | 9/2004 | Keller | |
| 2004/0215345 | A1 | 10/2004 | Perrone, Jr. et al. | |
| 2004/0220676 | A1 * | 11/2004 | Keller | 623/20.31 |
| 2004/0225368 | A1 * | 11/2004 | Plumet et al. | 623/20.15 |
| 2005/0027365 | A1 | 2/2005 | Burstein et al. | |
| 2005/0107883 | A1 * | 5/2005 | Goodfried et al. | 623/20.15 |
| 2005/0107886 | A1 | 5/2005 | Crabtree et al. | |
| 2005/0246028 | A1 | 11/2005 | Pappas et al. | |
| 2006/0265078 | A1 * | 11/2006 | McMinn | 623/20.14 |
| 2007/0078517 | A1 | 4/2007 | Engh et al. | |
| 2008/0021566 | A1 * | 1/2008 | Peters et al. | 623/20.16 |
| 2008/0058945 | A1 * | 3/2008 | Hajaj et al. | 623/20.14 |
| 2009/0005875 | A1 * | 1/2009 | Koenemann | 623/20.35 |
| 2009/0299482 | A1 * | 12/2009 | Metzger et al. | 623/20.29 |
| 2009/0319048 | A1 * | 12/2009 | Shah et al. | 623/20.29 |
| 2010/0174378 | A1 * | 7/2010 | Metzger et al. | 623/20.28 |

FOREIGN PATENT DOCUMENTS

| | | |
|---|---|---|
| DE | 3343606 | 7/1985 |
| DE | 19823325 | 3/2000 |
| EP | 1099430 | 9/1999 |
| EP | 1721584 | 5/2005 |
| FR | 2589720 | 11/1985 |
| FR | 2612767 | 9/1988 |
| FR | 2760352 | 9/1998 |
| WO | 8702883 | 5/1987 |
| WO | 0113825 | 3/2001 |
| WO | 0217821 | 3/2002 |

OTHER PUBLICATIONS

"Richards Modular Knee System", Richards Orthopedic catalog, 15 pgs, 1979.

"The femoropatellar endoprosthesis-still of value today?", Fink et al., Z Orthop Ihre Grenzgeb., 1999, May/June; 137 (3):247-52.

"Bicondylar St. George Sledge Knee Arthoplasty", Stockley et al., Clinical Orthopaedics and Related Research, No. 255, Jun. 1990, pp. 228-233.

"New Jersey Low Contact Stress Knee Replacement System", Buechel and Pappas, Surgical Reconstruction of the Arthritic Knee II, 1989.

"Patellofemoral Arthroplasty: A Three-to-Nine-Year Follow-up Study", Arciero et al, Clinical Orthopaedics and Related Research, No. 236, Nov. 1988, pp. 60-71.

"Kinematic I and Oxford Knee Arthroplasty-A 5-8-year FollowUp Study", Bourne et al., The Journal of Arthroplasty No. 4, Dec. 1987, pp. 285-291.

"Failed Polycentric Total Knee Prosthesis", Shoji et al., vol. 58-A, The Journal of Bone and Joint Surgery, No. 6, Sep. 1976, pp. 773-777.

European Search Report for European Patent Application No. 08165417.0-2310, Dec. 23, 2008, 8 pgs.

\* cited by examiner

Fig. 12

HINGED ORTHOPAEDIC PROSTHESIS

TECHNICAL FIELD

The present disclosure relates generally to orthopaedic prostheses, and particularly to constrained, hinged prosthesis for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the natural joint, orthopaedic prostheses of varying mobility may be used. For example, in cases involving significant bone loss or soft-tissue damage, a constrained orthopaedic prosthesis may be used. Constrained orthopaedic prostheses generally limit the mobility of the prosthetic joint to a single direction. One type of a constrained orthopaedic prosthesis is a hinged orthopaedic prosthesis.

SUMMARY

According to one aspect, an orthopaedic prosthesis may include a tibial bearing, a hinge post, and a femoral component. The tibial bearing may include an upper bearing surface. The upper bearing surface may include an aperture defined therein. The hinge post may include a base and a stem extending downwardly from the base and received in the aperture of the tibial bearing. The hinge post may also include a medial axle extending medially from the base and a lateral axle extending laterally from the base. A first bushing received on the medial axle. Additionally, a second bushing received on the lateral axle.

The femoral component may be configured to be coupled to a surgically-prepared surface of the distal end of a femur. The femoral component may include an articulating surface including a pair of spaced apart condyles in contact with the upper bearing surface of the tibial tray. Additionally, the femoral component may include an internal chamber having an opening defined on the articulating surface. The medial axle, lateral axle, first bushing, and second bushing may be received in the internal chamber. The femoral component may be configured to rotate about an axis defined by the medial and lateral axles. In some embodiments, the base of the hinge post may include a flange, which may be received in a recess defined in the articulating surface defined around the aperture of the tibial bearing.

The orthopaedic prosthesis may also include a plug in some embodiments. The plug may be received in the internal chamber of the femoral component and positioned to secure the femoral component to the hinged post. The first and second bushings may include a planar side in contact with the plug. In some embodiments, the plug is configured to restrict the first and second bushings from rotating with respect to the medial and lateral axles. Additionally, in some embodiments, the plug includes an angled anterior surface having a tab defined thereon and the internal chamber of the femoral component is defined by an anterior wall having a recess defined therein. In such embodiments, the tab of the plug being received in the recess. Additionally, in some embodiments, the internal chamber of the femoral component is defined by a medial wall and a lateral wall. The medial wall may include a first slot and the lateral wall may include a second slot. In such embodiments, the plug may include a medial side having a first rail received in the first slot and a lateral side having a second rail received in the second slot.

Additionally, in some embodiments, the plug may include an articulating outer surface substantially flush with the articulating surface of the femoral component. Alternatively, the plug may be received in the internal chamber of the femoral component such that the outer surface of the plug is recessed with respect to the articulating surface of the femoral component. Additionally, in some embodiments, the orthopaedic prosthesis may include a bolt and the plug may include an aperture defined therein. The bolt may be received in the aperture to secure the plug to the femoral component. Additionally, a cap may be received in the aperture of the plug and over the bolt. The cap may be positioned to contact a portion of the hinge post during hyperextension.

In some embodiments, the femoral component may be embodied as a housing and a patella bearing. The housing may include the pair of spaced apart condyles. The patella bearing may be separate from the housing, but secured thereto. The housing of the femoral component may include an anterior plate. In such embodiments, a portion of the patella bearing may be in contact with the anterior plate. The patella bearing may be configured to secure the femoral component to the hinge post.

Accordingly to another embodiment, an orthopaedic prosthesis may include a hinge post and a femoral component. The hinge post may include a base and a stem extending downwardly from the base. Additionally, the hinge post may include a medial axle extending medially from the base and a lateral axle extending laterally from the base. A first bushing may be received on the medial axle and a second bushing may be received on the lateral axle The femoral component may be configured to be coupled to a surgically-prepared surface of the distal end of a femur. The femoral component may have an internal chamber defined between a pair of condyles. The internal chamber may be defined by a medial wall having a first slot defined therein and a lateral wall having a second slot defined therein. The first bushing being may be received in the first slot and the second bushing may be received in the second slot.

The orthopaedic prosthesis may also include a plug received in the internal chamber of the femoral component and positioned to secure the femoral component to the hinged post. The first and second bushings include a planar side in contact with the plug. The plug may be configured to restrict the first and second bushings from rotating with respect to the medial and lateral axles. Additionally, the femoral component may include an articulating surface and the plug may include an articulating outer surface substantially flush with the articulating surface of the femoral component. In some embodiments, the plug may be received in the internal chamber of the femoral component such that an outer surface of the plug is recessed with respect to the articulating surface of the femoral component.

According to a further aspect, a hinged orthopaedic prosthesis may include a hinge post, a first bushing, a second bushing, an a femoral component coupled to the first bushing and the second bushing. The hinge post may include a base and a stem extending downwardly from the base. The hinge post may also include a first an second axle extending from the base. The first bushing may be received on the first axle and may include at least one flat side. The second bushing may be received on the second axle and may include at least one flat side. The femoral component may be configured to rotate about an axis defined by the first axle and the second axle.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIGS. 1-4, a hinged orthopaedic prosthesis 10 includes a tibial insert or bearing 12, a femoral component 14, and a hinge post 16 configured to be coupled to the insert bearing 12 and the femoral component 14. The tibial bearing 12 is illustratively formed from a polymer material, but may be formed from other materials, such as a ceramic material, a metallic material, a bio-engineered material, or the like, in other embodiments. The femoral component 14 and the hinge post 16 are illustratively formed from a metallic material such as cobalt-chromium or titanium, but may be formed from other materials, such as a ceramic material, a polymer material, a bio-engineered material, or the like, in other embodiments.

Figure 1:
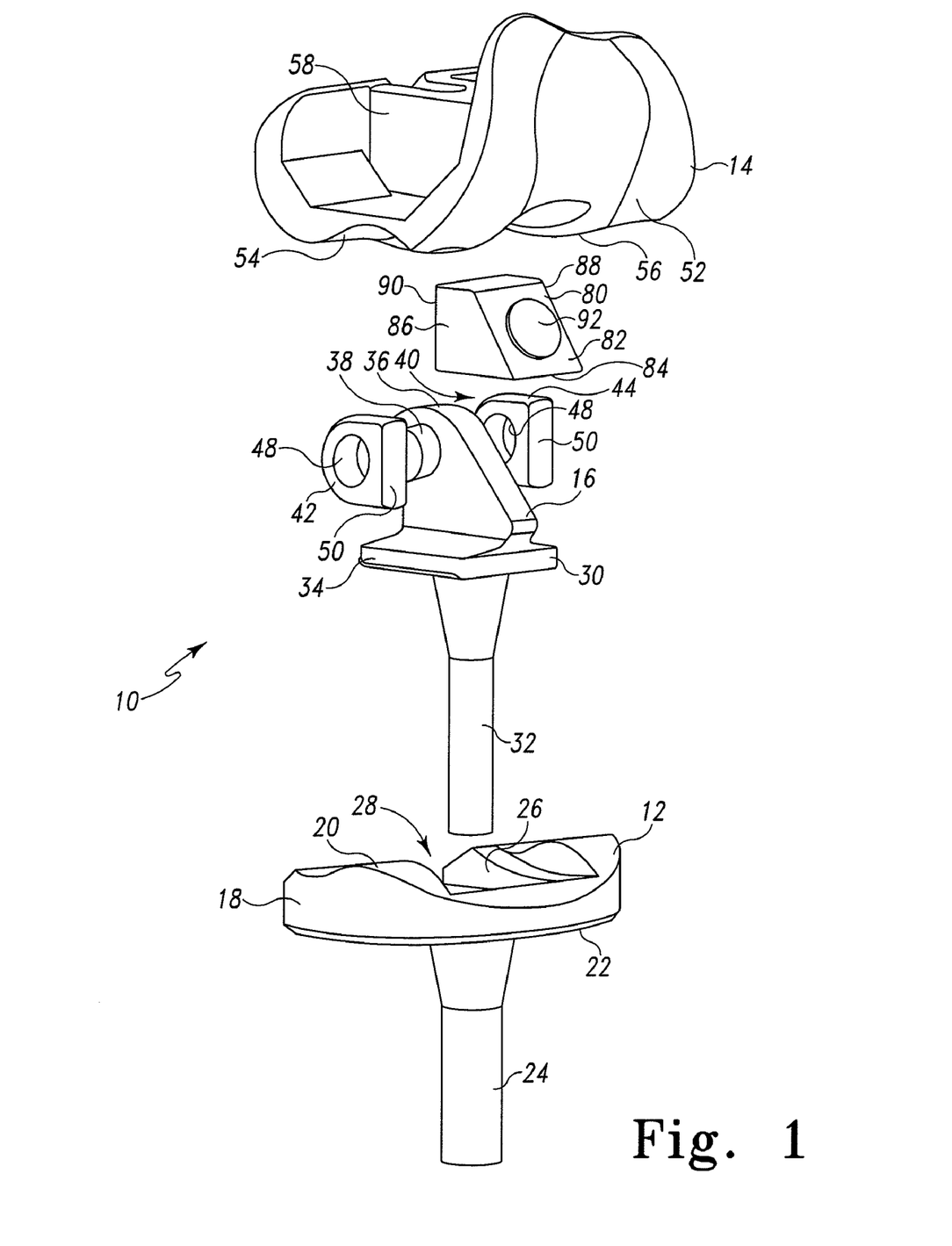
FIG. 1 is an exploded perspective view of one embodiment of a hinged orthopaedic prosthesis.

The tibial bearing 12 includes a platform 18 having an upper bearing surface 20 and a bottom surface 22. A stem 24 extends downwardly from the bottom surface 22 of the platform 18. The tibial bearing 12 is configured to be coupled to a tibial tray (not shown). When so coupled, the stem 24 of the tibial bearing 12 is received in an aperture of the tibial tray. In some embodiments, the tibial bearing 12 may be configured to rotate about an axis defined by the stem 24 relative to the tibial tray.

The upper bearing surface 20 of the tibia bearing 12 is configured to contact a pair of natural or prosthetic femoral condyles, such as the condyles 54, 56 of the femoral component 14 as discussed in more detail below. The upper bearing surface 20 includes a recess 26 defined therein. The recess 26 is shaped to receive a portion of a base 30 of the hinge post 16 as discussed below. The illustrative recess 26 has a substantially rectangular shape, but may have other shapes in other embodiments. An aperture 28 is defined in the recess 26 of the upper bearing surface 20. The aperture 28 is configured to receive a stem 32 of the hinge post 16.

The hinge post 16 includes a base 30 and a stem 32 extending downwardly therefrom. As discussed above, the stem 32 is configured to be received in the aperture 28 of the tibial bearing 12. The base 30 includes a flange 34 defined toward the bottom of the base 30. When the hinge post 16 is coupled to the tibial bearing 12, the flange 34 is received in the recess 26 of the bearing 12. As such, the flange 34 may have any shape corresponding to the shape of the recess 26. The base 30 of the hinge post 16 includes a mount 36. A pair of axles 38, 40 extend horizontally from the mount 36. In particular, a medial axle 40 extends from the mount 36 in the medial direction and a lateral axle 38 extends from the vertical mount 36 in the lateral direction. The axles 38, 40 extend from the mount 36 at a substantially orthogonal direction.

The orthopaedic prosthesis 10 also includes a pair of bushings 42, 44. The bushings 42, 44 are configured to be inserted onto the axles 38, 40. That is, each bushing 42, 44 includes an aperture 48 having a diameter slightly greater than the diameter of the respective axle 38, 40. As illustrated in FIG. 1, the bushings 42, 44 have a substantially "D"-shape. That is, each bushing 42, 44 has at least one flat or planar side surface 50. The bushings 42, 44 may be formed from any material that facilitates the rotation of the bushings around the axles 38, 40. For example, the bushings 42, 44 may be formed from a plastic material or the like. In one particular embodiment, the bushings 42, 44 are formed from ultra-high molecular weight polyethylene (UHMWPE).

The femoral component 14 is configured to be coupled to a surgically-prepared surface of the distal end of a patient's femur (not shown). The femoral component 14 may be secured to the patient's femur via use of bone adhesive or other attachment means. The femoral component 14 includes an articulating surface 52 having a pair of spaced apart condyles 54, 56. In use, the condyles 54, 56 replace the natural condyles of the patient's femur and are configured to articulate on the upper bearing surface 20 of the tibial insert 12.

Figure 2:
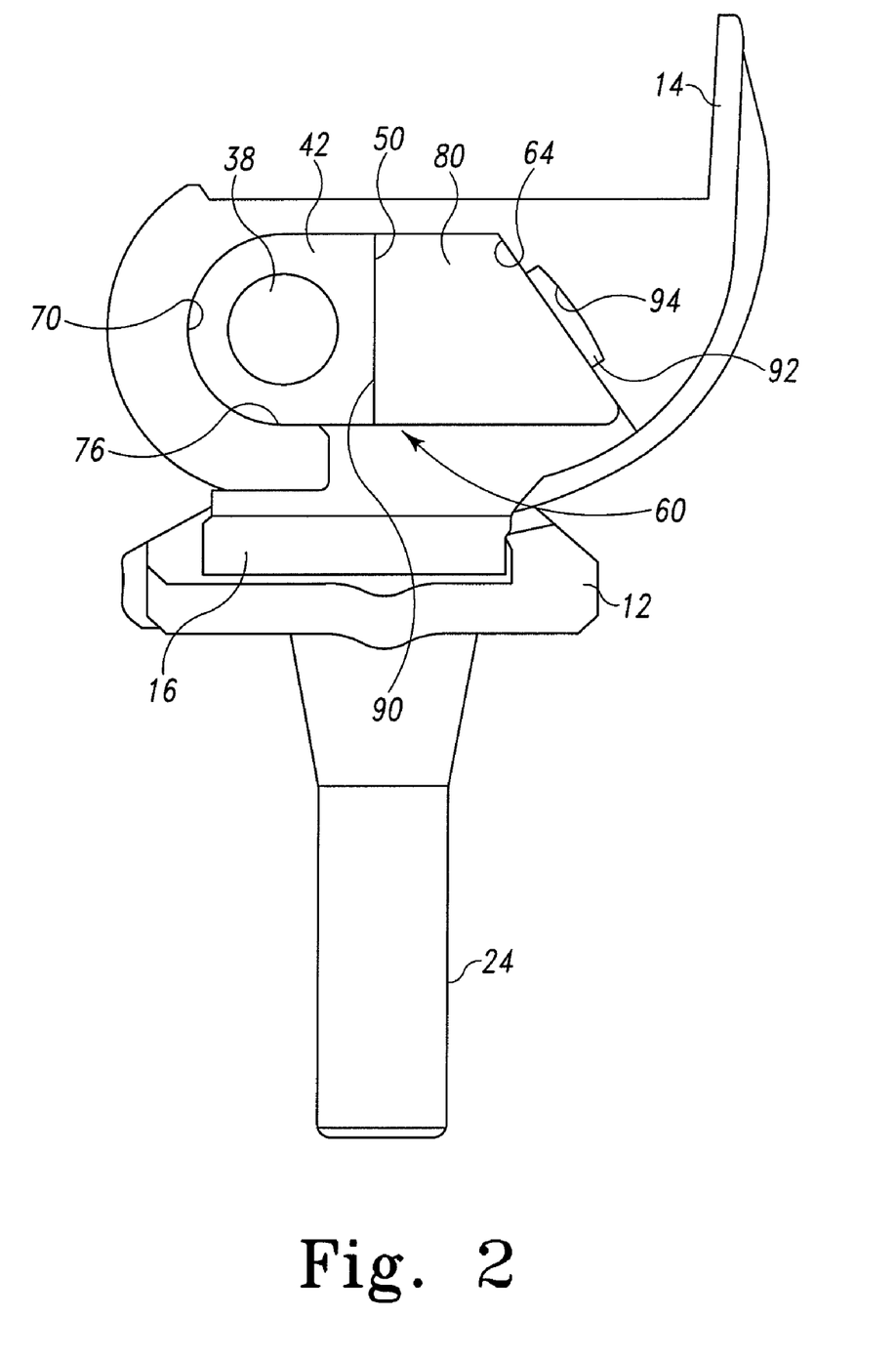
FIG. 2 is a side elevation, cross-sectional view of the hinged orthopaedic prosthesis of FIG. 1 in an assembled configuration.
Figure 3:
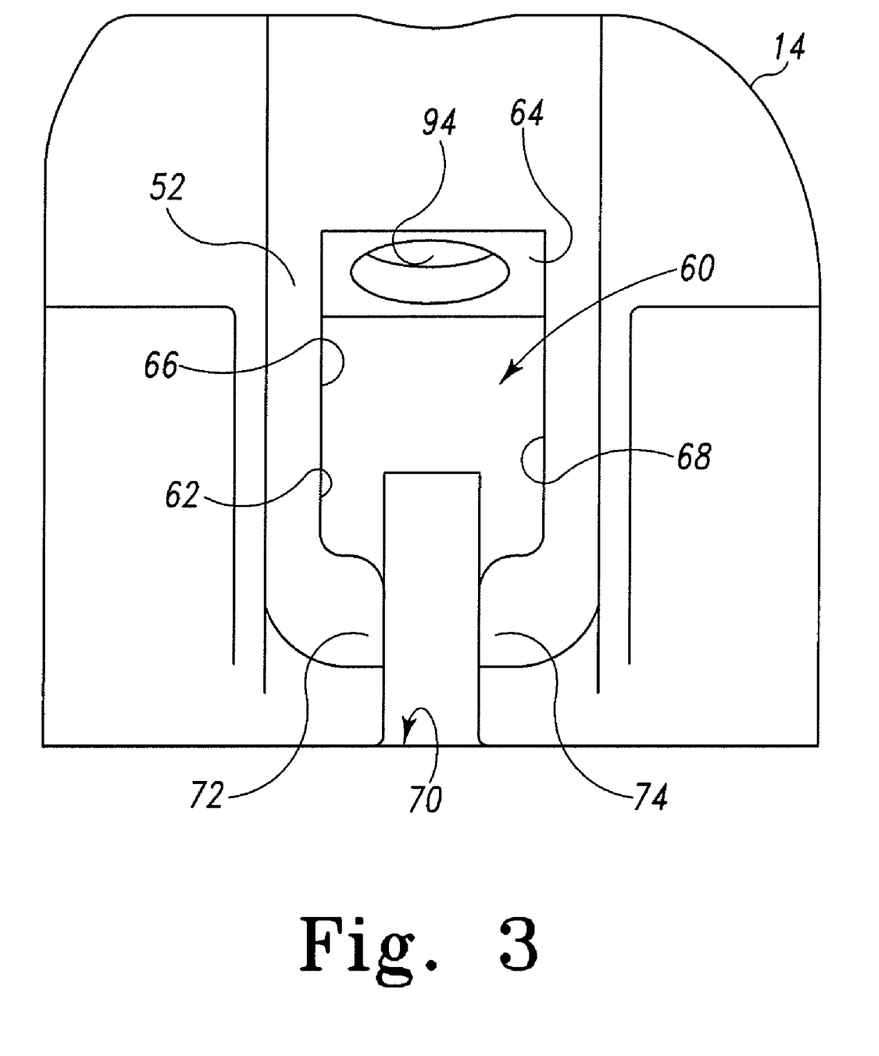
FIG. 3 is an elevation view of a femoral component of the hinged orthopaedic prosthesis of FIG. 1

The femoral component 14 includes a housing 58 having an internal chamber 60 (see FIGS. 2 and 3) defined therein. The internal chamber 60 includes an opening 62 defined in the articulating surface 52 of the femoral component 14. As shown in FIGS. 2 and 3, the illustrative internal chamber 60 of the femoral component 14 is rectangular in shape, but may have other shapes in other embodiments. The internal chamber 60 is defined by an anterior sidewall 64, a medial sidewall 66, a lateral sidewall 68, and a posterior sidewall 70. In some embodiments, the anterior sidewall 64 and/or the posterior sidewall 70 are angled. Additionally, as shown in FIG. 3, a portion of the articulating surface 32 extends over the opening 62 of the internal chamber 60 to define a pair of lips 72, 74. The lips 72, 74 define a posterior slot 76 of the internal chamber 60 (see FIG. 2).

The hinged orthopaedic prosthesis 10 may also include a plug 80. The plug 80 is insertable into the internal chamber 60 to secure the hinge post 10 and bushings 42, 44 to the femoral component 14. The plug 80 may have any shape configured to be received in the internal chamber 60 and secure the bushings 42, 44 therein. For example, as illustrated in FIG. 1, the plug 80 may include an anterior wall or surface 82, an outer wall or surface 84, a medial wall or surface 86, a lateral wall or surface 88, and posterior wall or surface 90. In the embodiment illustrated in FIG. 1, the anterior surface 82 of the plug 80 is angled and includes a tab 92 defined thereon. Illustratively, the tab 92 has a circular shape, but tabs having other shapes may be use in other embodiments.

In use, the femoral component 14 is coupled to the hinge post 16, which is coupled to the tibial insert 12. To do so, the stem 32 of the hinge post 16 may be inserted into the aperture 28 of the tibial insert 12. The flange 34 of the base 30 of the hinge post 16 is received in the recess 26 before the hinge post 16 is fully seated on the tibial bearing 12. In some embodiments, the recess 26 is larger than the flange 34 to allow positioning of the hinge post 16 and increase the load transfer from the femoral condyles 54, 56 to the upper bearing surface 20 of the tibial bearing 12. The bushings 42, 44 may also be inserted onto the medial and lateral axles 38, 40 of the hinge post 16.

The femoral component 14 may be secured to the hinge post 16. To do so, the base 30, the axles 38, 40, and the bushings 42, 44 are inserted vertically into the internal chamber 60 of the femoral component 14. Once so inserted, the femoral component 14 is moved in the anterior direction until the bushings 42, 44 are received in the posterior slots 76 of the internal chamber 60 as illustrated in FIG. 2. It should be appreciated that the posterior wall 70 of the femoral component 14 defining the internal chamber 60 may have a shape corresponding to the bushings 42, 44. For example, the illustrative posterior wall 70 has a curved shape matching the generally curved shape of the bushings 42, 44 as shown in FIG. 2.

After the axles 38, 40 and bushings 42, 44 have been inserted into the internal chamber 60 of the femoral component 60; the plug 80 may be coupled to the femoral component 14 to secure the hinge post 16 and the femoral component 14 together. To do so, the plug 80 is inserted into the internal chamber 60. Depending on the configuration of the plug 80, the plug 80 may be held in place via tabs, friction, securing devices, or the like. For example, in the embodiment illustrated in FIG. 1, the tab 92 of the plug 80 is received in an aperture 94 defined in the anterior wall 64 of the internal chamber 60 (see FIGS. 2 and 3). The tab 92 and aperture 94 cooperate to form a friction lock therebetween to hold the plug 80 in place. As shown in FIG. 2, when the plug 80 is inserted into the internal chamber 60, the posterior wall 90 of the plug 80 contacts the planar side surface 50 of the bushings 42, 44. As such, the bushings 42, 44 are restricted from rotating and, in some embodiments, translating relative to the femoral component 14. Because only the bushings 42, 44 rotate only with respect to the axles 38, 40, micro-motion between the axles 38, 40, bushings 42, 44, and the femoral component 14 may be reduced.

Figure 4:
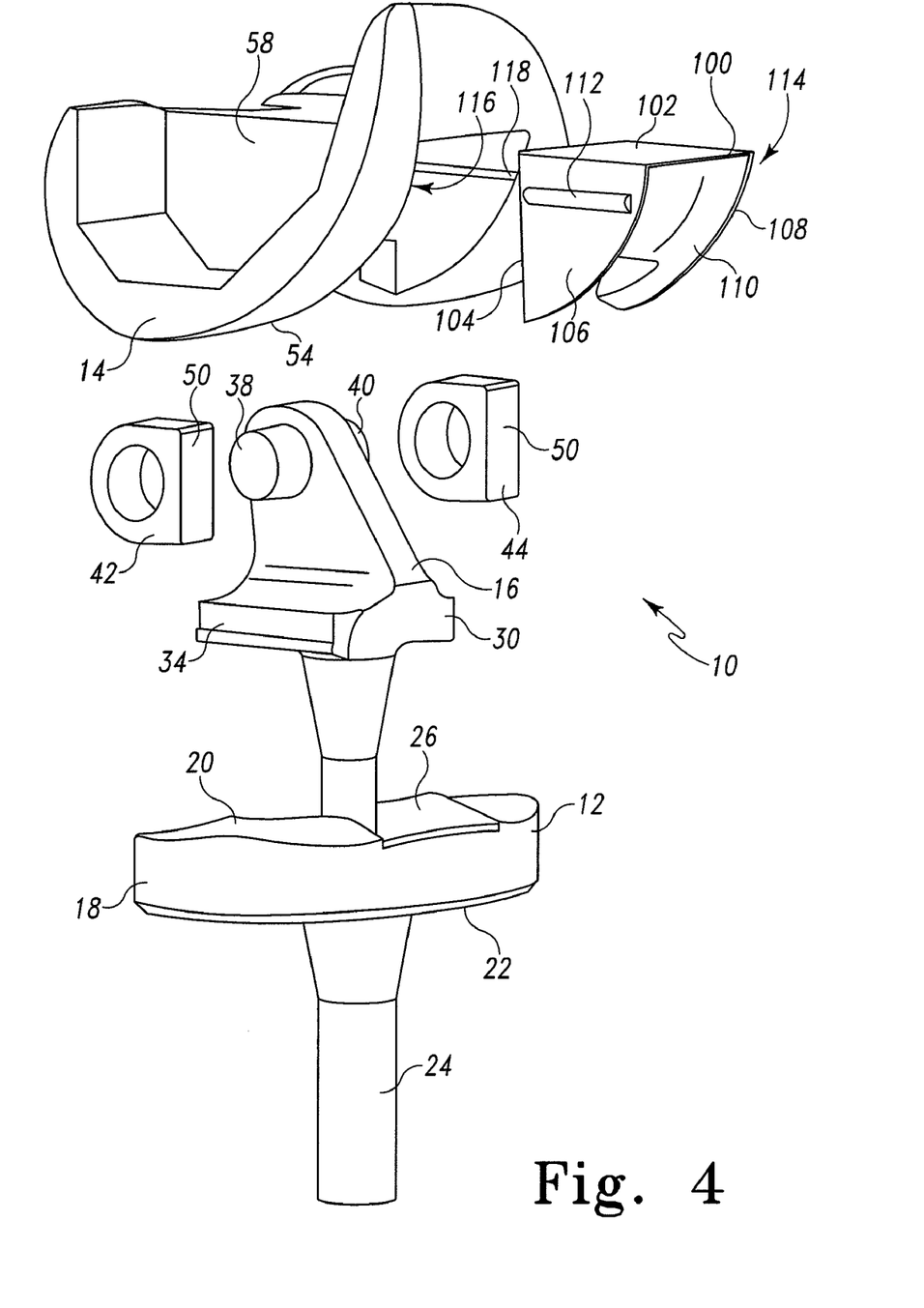
FIG. 4 is an exploded perspective view of another embodiment of a hinged orthopaedic prosthesis.

Referring now to FIG. 4, as discussed above, the plug 80 may have any one of a number of configurations and shapes. For example, a plug 100 may be used with the orthopaedic prosthesis 10. The plug 100 has a substantially triangular shape. That is the plug 100 has a planar proximal wall or surface 102, a planar rear wall or surface 104, a medial wall or surface 106, a lateral wall or surface 108, and a curved outer surface 110. The curved outer surface 110 of the plug 100 forms an articulating surface configured to contact the artificial or natural patella of a patient's knee. That is, during use, the patient's patella articulates across the outer surface 110. However, in other embodiments, the outer surface of the plug 80, 100 may not be configured as an articulating surface. For example, referring back to FIG. 2, the outer surface of the plug 80 is configured to be recessed into the internal chamber 60 relative to the articulating surface 52 of the femoral component 14 when the plug 80 is inserted therein. As such, the outer surface 52 of the plug 80 does not contact the patella of the patient during use.

Referring back to FIG. 4, the plug 100 may include a medial rail 112 defined on the medial wall 106 and a lateral rail 114 defined on the lateral wall 108. The rails 106, 108 are positioned and oriented on the walls 106, 108 such that the rails 112, 114 are received in corresponding slots 116, 118 defined in the medial wall 66 and lateral wall 68 of the femoral component 14, which define the internal chamber 60. That is, plug 100 may be configured to be coupled to the femoral component 14 by inserting the rails 112, 114 into the slots 116, 118 and sliding the plug 100 into the internal chamber 60. As discussed above, when the plug 100 is so inserted, the outer surface 110 is substantially parallel with the articulating surface 52 of the femoral component 14 and forms an articulating surface for the patient's patella.

Figure 5:
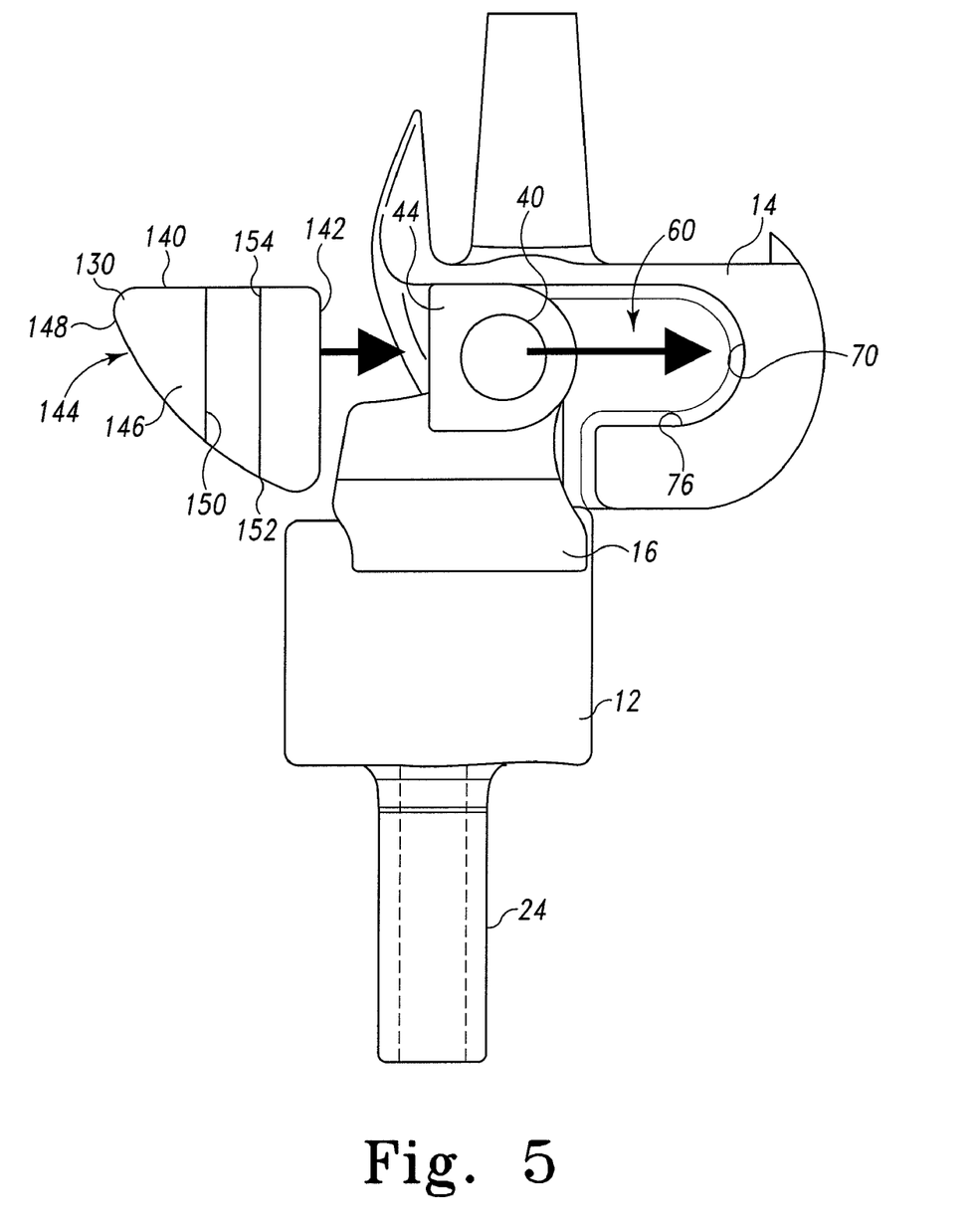
FIG. 5 is an exploded cross-sectional view of another embodiment of a hinged orthopaedic prosthesis.
Figure 6:
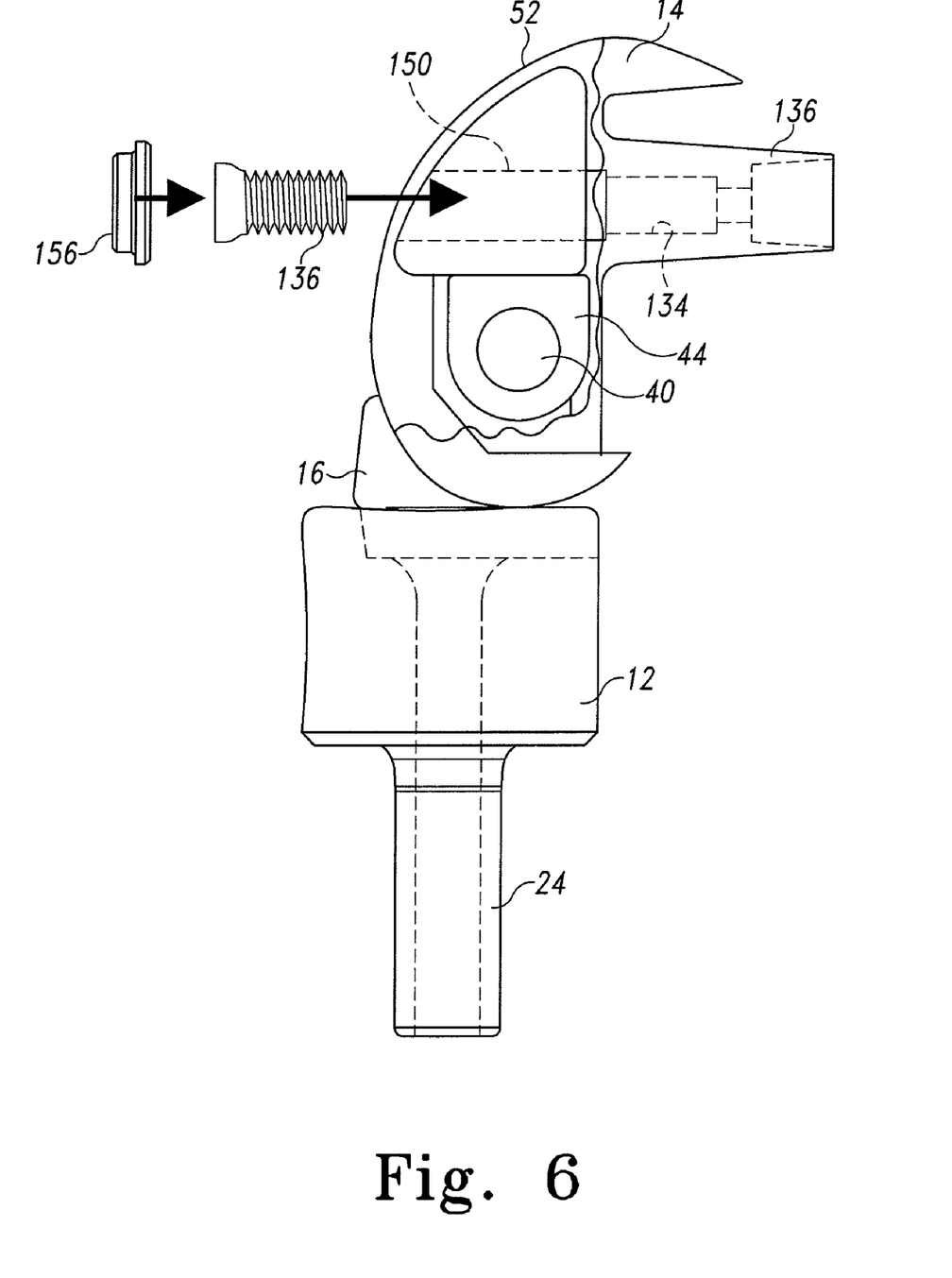
FIG. 6 is a side elevation view of the hinged orthopaedic prosthesis of FIG. 5.

Referring now to FIGS. 5-8, in another embodiment, a plug 130 is configured to be secured to the femoral component 14 via a securing device 132 such as a screw or bolt. In such embodiments, the housing 58 of the femoral component 14 includes a threaded aperture 134 defined in a stem 136, which extends upwardly from the housing 58 as shown in FIG. 6. The illustrative plug 130 has a shape similar to the plug 100 illustrated in and described above in regard to FIG. 4. The plug 130 has a planar proximal wall or surface 140, a planar posterior wall or surface 142, a medial wall or surface 144, a lateral wall or surface 146, and an outer surface 148, which may be angled or curved in some embodiments. The plug 130 also includes an aperture 150 defined therethrough and having an opening 152 on the outer surface 148 and the proximal surface 140.

Figure 8:
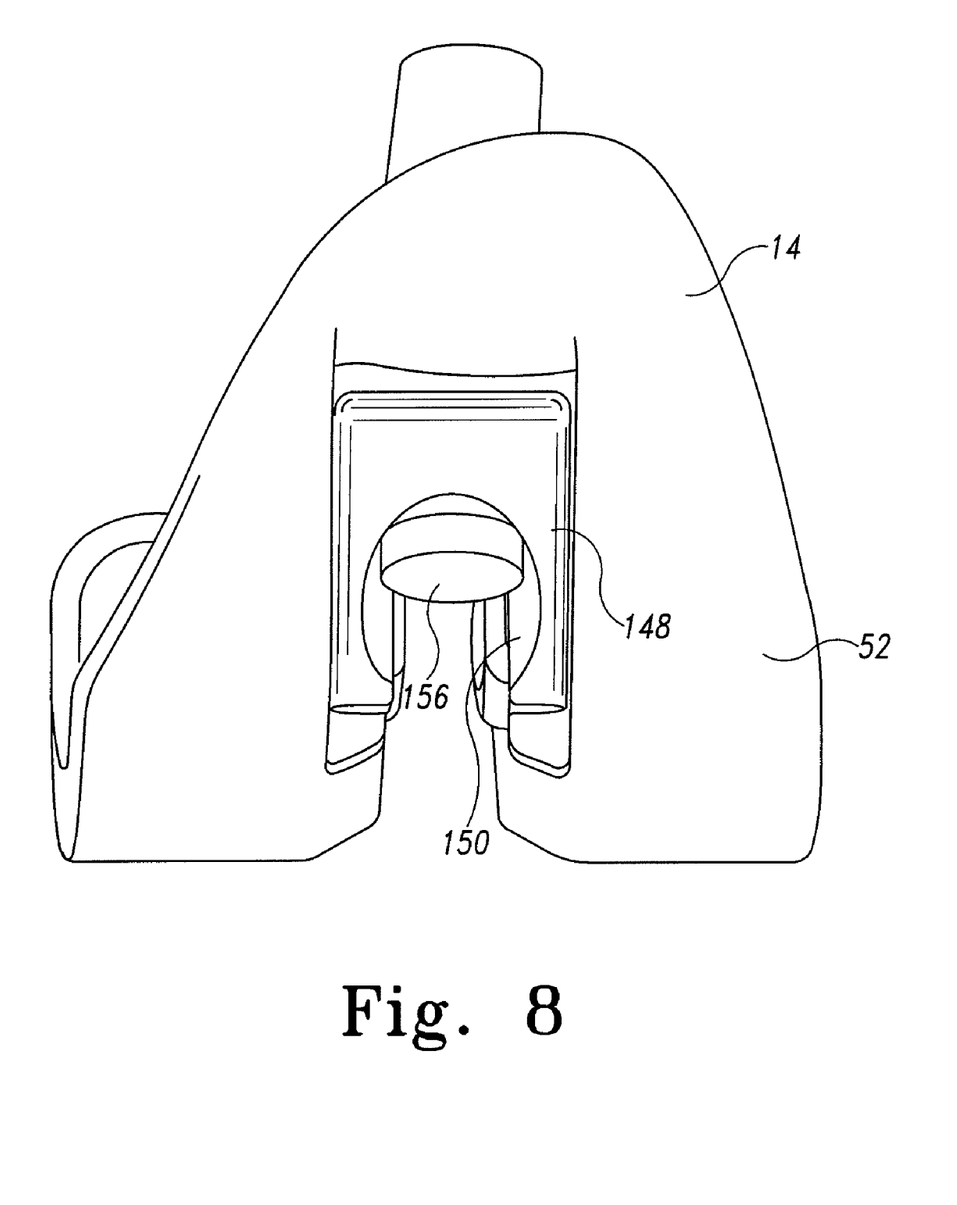
FIG. 8 is elevation view of another embodiment of a femoral component of the hinged orthopaedic prosthesis of FIG. 5.

As shown in FIG. 5, the plug 130 may be inserted into the internal chamber 60 by positioning the orthopaedic prosthesis 10 in extension. After the plug 130 has been inserted into the internal chamber 60, the orthopaedic prosthesis (or the patient's leg) may be positioned in flexion, such as 90 degrees of flexion, as illustrated in FIG. 8. A screw or bolt 154 may be inserted into the aperture 150 defined in the plug 130 and threaded into the threaded aperture 134 of the femoral component 14. After the bolt 154 has been inserted into the aperture 150 and secured to the femoral component 14, a cap 156 may be inserted into the end of the aperture 150 over the bolt 154. The cap 156 may be formed from any suitable material such as, for example, a polyethylene material. During use, the cap 156 forms a type of bumper to restrict the prosthesis 10 from being positioned past some predetermined degree of hyperextension. That is, the cap or bumper 156 is configured and positioned relative to the femoral component 14 such that the cap 156 contacts a portion of the hinge post 16 and/or tibial bearing 12 at some amount of hyperextension. The particular degree of hyperextension at which the cap 156 contacts the hinge post 16 and/or bearing 12 may be determined based on the design and configuration of the cap 156. For example, a larger cap 156 may be used in some embodiments.

Figure 7:
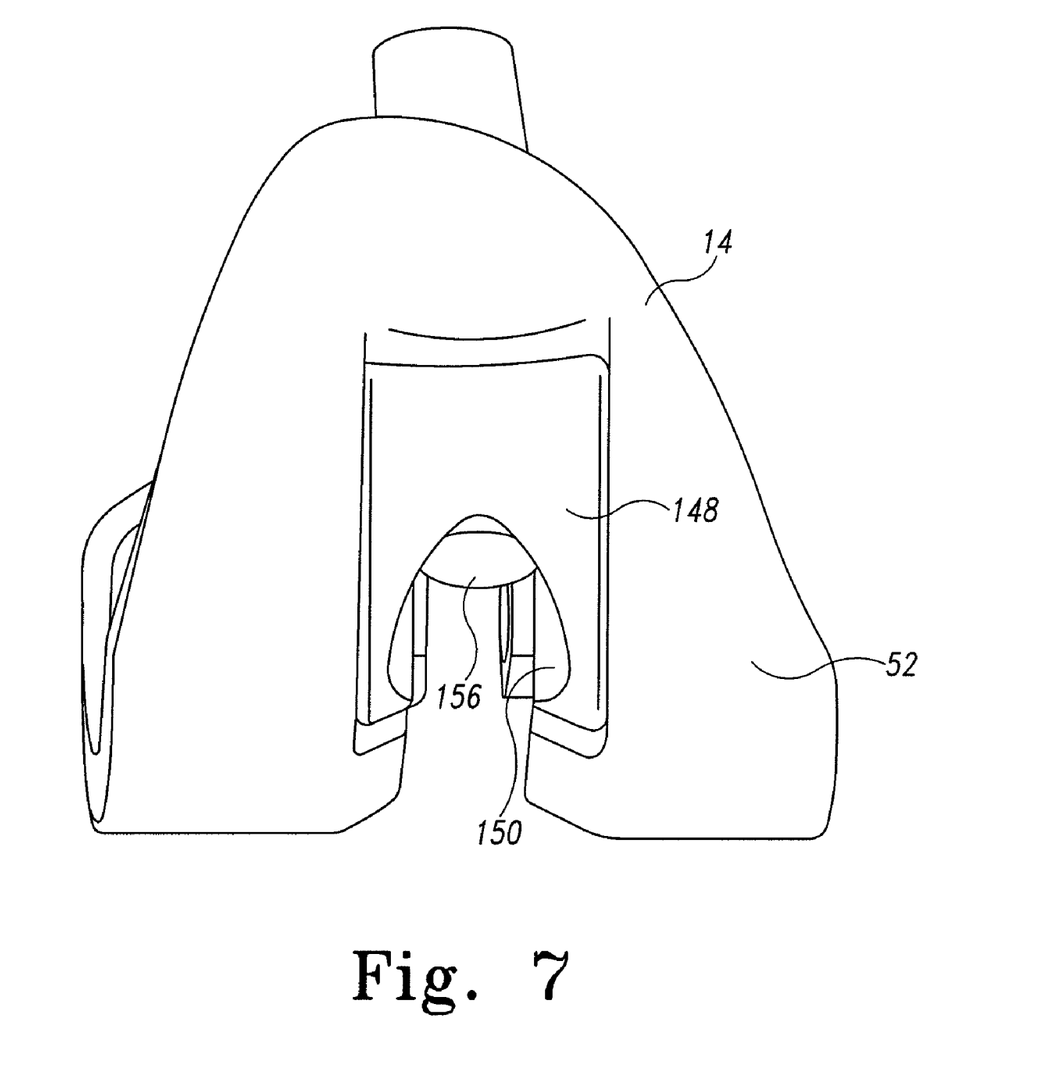
FIG. 7 is an elevation view of one embodiment of a femoral component of the hinged orthopaedic prosthesis of FIG. 5.

The outer surface or wall 148 of the plug 130 may be configured as an articulating surface in some embodiments. For example, as illustrated in FIG. 7, the outer surface 148 of the plug 130 is curved and forms an articulating surface configured to contact the natural or artificial patella of a patient's knee. That is, during use, the patient's patella articulates across the outer surface 148 of the plug 130. However, in other embodiments, the outer surface 148 of the plug 130 may not be configured as an articulating surface. For example, as illustrated in FIG. 8, the outer surface 148 of the plug 130 is configured to be recessed into the internal chamber 60 relative to the articulating surface 52 of the femoral component 14 when the plug 130 is inserted and secured therein. As such, the outer surface 148 of the plug 130 does not contact the patella of the patient during use.

Referring now to FIGS. 9-12, in another embodiment, the femoral component 14 of the orthopaedic prosthesis 10 includes a housing 160 and a patella bearing 162 configured to be coupled to the housing 160. The housing 160 includes the condyles 54, 56 and the internal chamber 60. The patella bearing 162 includes an outer articulating surface 164 configured to contact the patient's natural or artificial patella during use. An aperture 166 is defined in the articulating surface 164 and configured to receive a bolt, screw, or other securing 168 means as discussed below.

Figure 9:
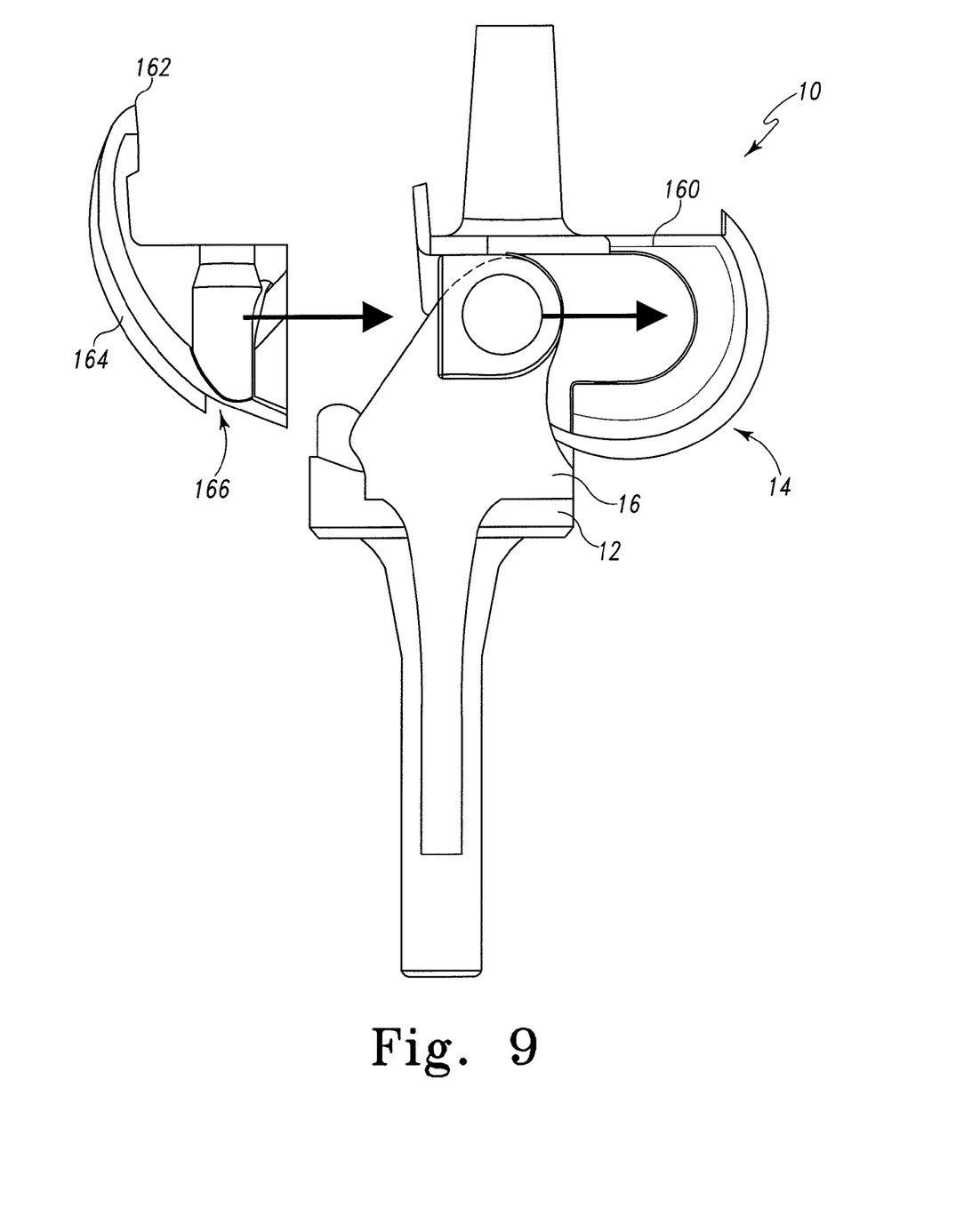
FIG. 9 is an exploded cross-sectional view of another embodiment of a hinged orthopaedic prosthesis.

When the patella bearing 162 is removed from the housing 160, the internal chamber 60 is accessible. As such, the femoral component 14 may be coupled and secured to the hinge post 16 by initially removing the patella bearing 162. The femoral component 14 may then be positioned in an extended position. The mount 36 of the hinge post 16, axles 38, 40, and bushings 42, 44 may then be slid horizontally into the internal chamber 60 as illustrated in FIG. 9. After the hinge post 16, axles 38, 40, and bushings 42, 44 are received in the internal chamber 60, the patella bearing 162 may be coupled to the housing 160 of the femoral component 14. In some embodiments, the patella bearing 162 and housing 160 may include corresponding rails and/or guides to facilitate the coupling of the patella bearing 162 to the housing 160. It should be appreciated that in one particular embodiment, the orthopaedic prosthesis is designed such that the patella bearing 162 is removable from the housing 160 only during hyperextension. That is, the patella bearing 162 may be removed from the housing 160 only while the orthopaedic prosthesis 10 is in a degree of hyperextension, which is selected to be greater than the normal allowable patient range of motion of the assembled orthopaedic prosthesis 10.

Figure 10:
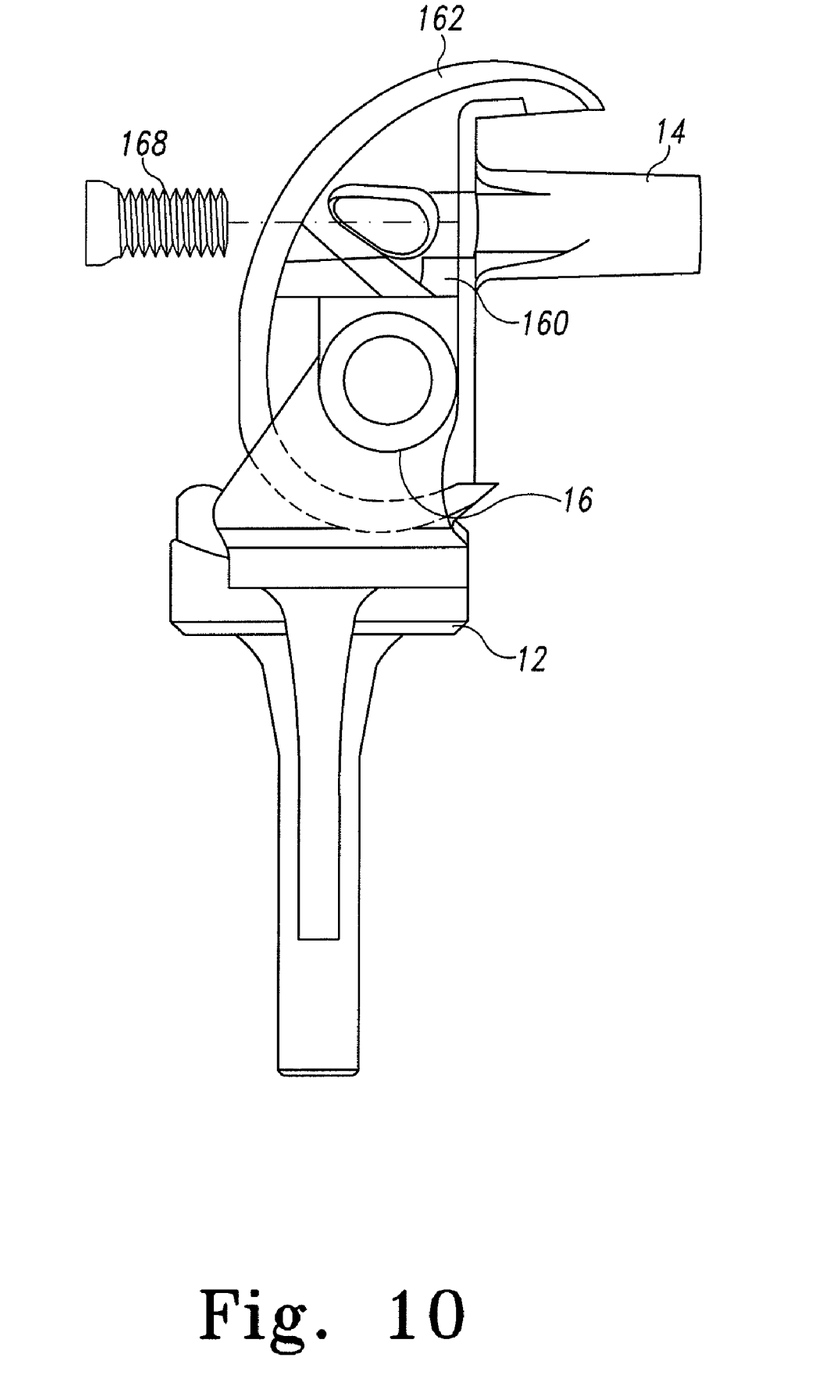
FIG. 10 is a side elevation, cross-sectional view of the hinged orthopaedic prosthesis of FIG. 9.

The patella bearing 162 may be secured to the housing 160 via use of the bolt 168. That is, as illustrated in FIG. 10, the orthopaedic prosthesis 10 may be moved to a flexed position such that the bolt 168 may be inserted into the aperture 166 of the patella bearing 162 and threaded into the housing 160 of the femoral component 14.

Figure 11:
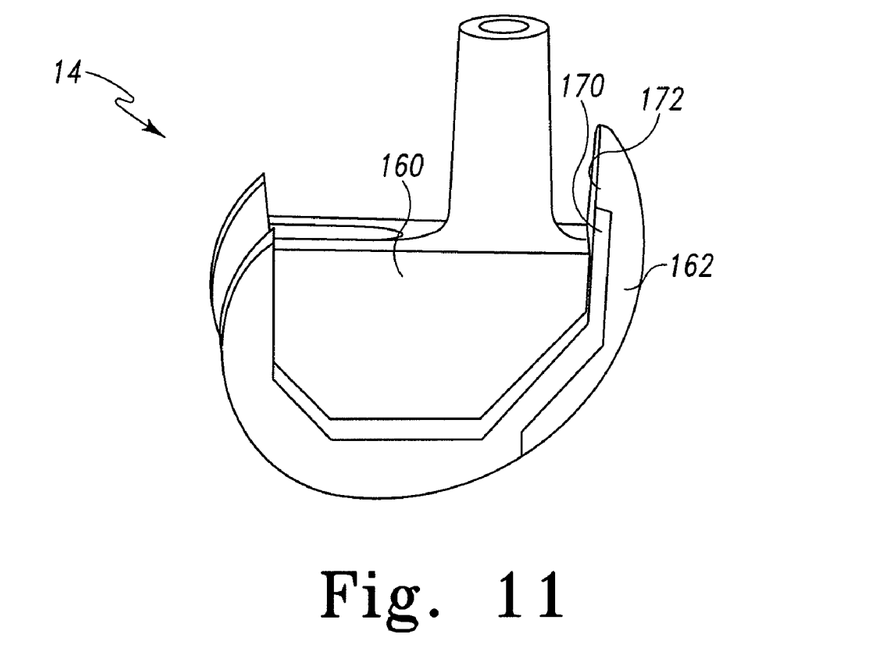
FIG. 11 is an elevation view of one embodiment of a femoral component of the hinged orthopaedic prosthesis of FIG. 9.
Figure 12:
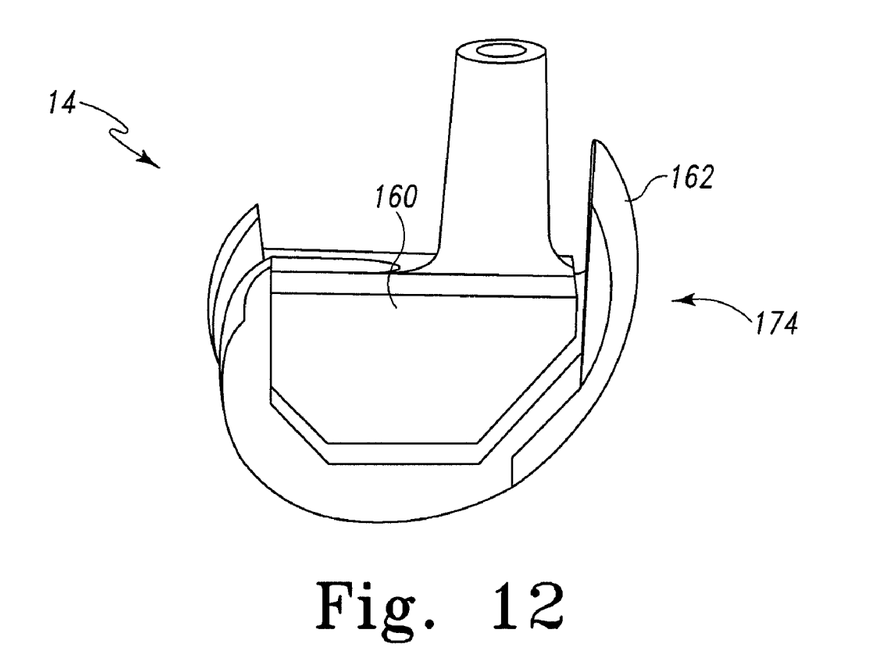
FIG. 12 is an elevation view of another embodiment of a femoral component of the hinged orthopaedic prosthesis of FIG. 9.

The interface between the patella bearing 162 and the housing 160 of the femoral component 14 may vary in different embodiments. For example, as illustrated in FIG. 11, in one embodiment, the housing 160 of the femoral component 14 includes an anterior plate 170 on which a portion of the patella bearing 162 is received. Additionally, the patella bearing 162 includes a lip 172 in such embodiments. The lip 172 overlaps the proximal end of the anterior plate 170 when the patella bearing 162 is coupled to the housing 160. Alternatively, as illustrated in FIG. 12, the housing 160 of the femoral component 14 may not include the anterior plate 170. In such embodiments, an anterior portion 174 of the patella bearing 162 has an increased thickness to support the articulation of the patella thereon.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthesis comprising:
a tibial bearing having an upper bearing surface including an aperture defined therein;
a hinge post including a base, a stem extending downwardly from the base and received in the aperture of the tibial bearing, a medial axle extending medially from the base, and a lateral axle extending laterally from the base;
a first bushing having a first curved surface received on the medial axle and a second bushing having a second curved surface received on the lateral axle;
a femoral component configured to be coupled to a surgically-prepared surface of the distal end of a femur, the femoral component having (i) an articulating surface including a pair of spaced apart condyles in contact with the upper bearing surface of the tibial tray, (ii) a medial sidewall extending from the articulating surface, (iii) a lateral sidewall extending from the articulating surface, (iv) a pair of curved sidewalls positioned between the lateral sidewall and the medial sidewall, and (v) an internal chamber defined by the medial sidewall, the lateral sidewall, and the pair of curved sidewalls, the internal chamber having an opening defined on the articulating surface,
wherein (i) the medial axle, lateral axle, first bushing, and second bushing are received in the internal chamber, (ii) the pair of curved sidewalls receive the first curved surface of the first bushing and the second curved surface of the second bushing, and (iii) the femoral component is configured to rotate about an axis defined by the medial and lateral axles.

2. The orthopedic prosthesis of claim 1, wherein the base of the hinge post includes a flange and the tibial bearing includes a recess in the articulating surface defined around the aperture, the flange of the base of the hinge post being received in the recess of the tibial bearing.

3. The orthopaedic prosthesis of claim 1, further comprising a plug received in the internal chamber of the femoral component and positioned to secure the femoral component to the hinged post.

4. The orthopaedic prosthesis of claim 3, wherein each of the first and second bushings includes a planar side in contact with the plug.

5. The orthopedic prosthesis of claim 3, wherein the plug is configured to restrict the first and second bushings from rotating with respect to the medial and lateral axles.

6. The orthopaedic prosthesis of claim 3, wherein:
the plug includes an angled anterior surface having a tab defined thereon, and
the internal chamber of the femoral component is further defined by an anterior wall having a recess defined therein, the tab of the plug being received in the recess.

7. The orthopaedic prosthesis of claim 3, wherein:
the medial sidewall of the femoral component includes a first slot defined therein and the lateral sidewall of the femoral component includes a second slot defined therein, and
the plug includes a medial side and a lateral side, a first rail being defined on the medial side and a second rail being defined on the lateral side, the first rail being received in the first slot and the second rail being received in the second slot.

8. The orthopaedic prosthesis of claim 3, wherein the plug includes an articulating outer surface substantially flush with the articulating surface of the femoral component.

9. The orthopaedic prosthesis of claim 3, wherein the plug includes an outer surface, the plug being received in the internal chamber of the femoral component such that the outer surface of the plug is recessed with respect to the articulating surface of the femoral component.

10. The orthopaedic prosthesis of claim 3, further comprising a bolt, wherein the plug includes an aperture defined therein, the bolt being received in the aperture and securing the plug to the femoral component.

11. The orthopaedic prosthesis of claim 10, further comprising a cap received in the aperture of the plug and positioned over the bolt.

12. The orthopaedic prosthesis of claim 11, wherein the cap is positioned to contact a portion of the hinge post during hyperextension.

13. The orthopaedic prosthesis of claim 1, wherein the femoral component comprises (i) a housing including the pair of spaced apart condyles and a (ii) patella bearing separate from the housing, the patella bearing being secured to the housing.

14. The orthopaedic prosthesis of claim 13, wherein the housing of the femoral component includes an anterior plate, a portion of the patella bearing being in contact with the anterior plate.

15. The orthopaedic prosthesis of claim 14, wherein the patella bearing is configured to secure the femoral component to the hinge post.

16. An orthopaedic prosthesis comprising:
a hinge post including a base, a stem extending downwardly from the base, a medial axle extending medially from the base, and a lateral axle extending laterally from the base;
a first bushing received on the medial axle and a second bushing received on the lateral axle; and
a femoral component configured to be coupled to a surgically-prepared surface of the distal end of a femur, the femoral component having an internal chamber defined between a pair of condyles, the internal chamber being defined by (i) a medial wall having a first slot defined therein, the first slot having a first length defined in the anterior-posterior direction and a first width defined in the inferior-superior direction, the first length being greater than the first width, and (ii) a lateral wall having a second slot defined therein, the second slot extending parallel to the first slot and having a second length defined in the anterior-posterior direction and a second width defined in the inferior-superior direction, the second length being greater than the second width,
wherein the first bushing is received in the first slot and the second bushing being received in the second slot.

17. The orthopaedic prosthesis of claim 16, further comprising a plug received in the internal chamber of the femoral component and positioned to secure the femoral component to the hinged post.

18. The orthopaedic prosthesis of claim 17, wherein the first and second bushings include a planar side in contact with the plug.

19. The orthopedic prosthesis of claim 17, wherein the plug is configured to restrict the first and second bushings from rotating with respect to the medial and lateral axles and translating with respect to the femoral component.

20. The orthopaedic prosthesis of claim 17, wherein femoral component includes an articulating surface and the plug includes an articulating outer surface substantially flush with the articulating surface of the femoral component.

21. The orthopaedic prosthesis of claim 17, wherein femoral component includes an articulating surface and the plug includes an outer surface, the plug being received in the internal chamber of the femoral component such that the outer surface of the plug is recessed with respect to the articulating surface of the femoral component.

22. A hinged orthopaedic prosthesis comprising:
a hinge post including a base, a stem extending downwardly from the base, a first axle extending from the base, and a second axle extending from the base;
a first bushing received on the first axle and having a first curved surface and a first flat side;
a second bushing received on the second axle and having a second curved surface and a second flat side; and
a femoral component including a pair of curved sidewalls that define an internal chamber, the pair of curved sidewalls receiving the first curved surface of the first bushing and the second curved surface of the second bushing, the femoral component being configured to rotate about an axis defined by the first axle and the second axle, and
a plug secured to the femoral component and positioned in the internal chamber, the plug contacting the first flat side of the first bushing and the second flat side of the second bushing.

* * * * *